US006532891B2

(12) United States Patent
Gaugler et al.

(10) Patent No.: US 6,532,891 B2
(45) Date of Patent: Mar. 18, 2003

(54) APPARATUS AND METHOD FOR SEPARATION OF NEMATODES FROM SUSPENSION

(75) Inventors: Randy Gaugler, North Brunswick, NJ (US); Ian Brown, Americus, GA (US)

(73) Assignee: Rutgers, the State University, New Brunswick, NJ (US)

(*) Notice: Subject to any disclaimer, the term of this patent is extended or adjusted under 35 U.S.C. 154(b) by 0 days.

(21) Appl. No.: 10/156,327

(22) Filed: May 24, 2002

(65) Prior Publication Data

US 2003/0010293 A1 Jan. 16, 2003

Related U.S. Application Data

(63) Continuation-in-part of application No. 09/845,816, filed on Apr. 30, 2001, now Pat. No. 6,474,259.

(51) Int. Cl.⁷ ............................................. A01K 29/00
(52) U.S. Cl. ...................................................... 119/6.7
(58) Field of Search ................................. 119/6.5, 6.6

(56) References Cited

U.S. PATENT DOCUMENTS

| 5,023,183 | A | * | 6/1991 | Friedman et al. ............. 119/6.7 |
| 5,178,094 | A | | 1/1993 | Carr et al. .................... 119/6.5 |
| 5,554,533 | A | | 9/1996 | Bedding et al. ......... 435/252.1 |
| 5,694,883 | A | * | 12/1997 | Tachibana et al. ............ 119/6.7 |
| 6,223,687 | B1 | * | 5/2001 | Windle ........................ 119/6.7 |

* cited by examiner

*Primary Examiner*—Charles T. Jordan
*Assistant Examiner*—Elizabeth Shaw
(74) *Attorney, Agent, or Firm*—Licata & Tyrrell P.C.

(57) ABSTRACT

An apparatus and method for separating nematodes from an aqueous suspension is provided.

6 Claims, 1 Drawing Sheet

APPARATUS AND METHOD FOR SEPARATION OF NEMATODES FROM SUSPENSION

Figure 1:
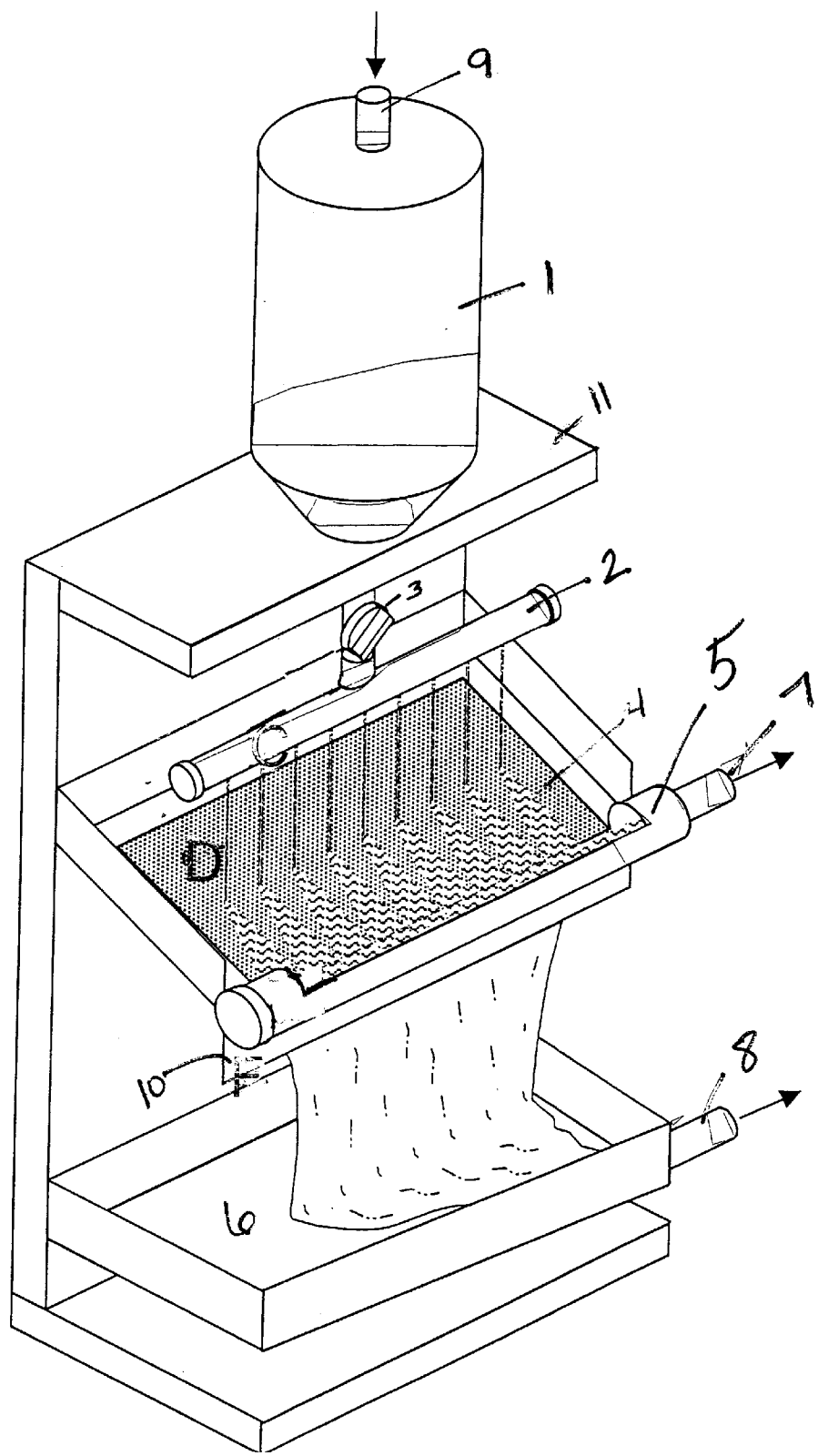

This application is a continuation-in-part of U.S. patent application No. 09/845,816 filed Apr. 30, 2001 now U.S. Pat. No. 6,474,259.

FIELD OF THE INVENTION

This invention relates to the field of agriculture and biological control of insect pests. In particular, the invention provides an apparatus and method for low-cost mass production of insecticidal nematodes.

BACKGROUND OF THE INVENTION

Heightened awareness of the dangers of chemical insecticides, combined with passage of the Federal Food Quality Protection Act restricting usage of these insecticides, has further increased the need for alternative insect control measures. Use of biological insecticides, in particular entomopathogenic nematodes, are consequently becoming an increasingly viable alternative to control insect pest populations.

Nematodes are simple, colorless, unsegmented roundworms that lack appendages. They may be free-living, predaceous or parasitic. The entomopathogenic nematodes of the genera Steinernema and Heterorhabditis are insect parasitic nematodes that possess an optimal balance of attributes to enable their use as biological control agents for insect pests.

Steinernema and Heterorhabditis have similar life cycles. The non-feeding infective juvenile seeks out insect hosts and penetrate into the insect body. There the juvenile releases a symbiotic bacterium, (i.e., Xeneorhabdus for steinernematids, Photorhadbdus for heterorhabditids), which multiplies rapidly and causes insect death. The nematodes feed upon the bacteria and liquefying insect, and mature into adults. The life cycle is completed in a few days, and hundreds of thousands of new infective juveniles emerge from the insect cadaver in search of fresh insect hosts.

Numerous benefits are derived by the use of nematodes as opposed to chemical insecticides or other biological methods. For example, nematodes are lethal to a greater number of important soil insect pests but are completely safe for plants and animals. Further, most chemical insecticides and biologicals require days or even weeks to kill insect pests, whereas nematodes usually kill most insect pests within 24–48 hours.

The two genera of entomopathogenic nematodes comprise nearly 30 species that are useful as biological control agents against a large number of insect pests, including artichoke plume moth, root weevils, cranberry girdler, sciarids, wood borers, fungus gnats, scarabs, mole crickets, billbugs, army worms, cut worms and web worms.

Unfortunately, for nematodes to represent a commercially viable alternative to chemical insecticides a self-contained, low cost system of production is preferable, if not necessary. Current methods of nematode production require tedious multi-step procedures involving sterilization techniques and expensive equipment, resulting in high production costs and contamination problems.

Moreover, although some of the above-described systems have been used on a small scale, a major difficulty arises when scale-up of nematode production is attempted. In vivo systems have proven difficult to scale-up. In the laboratory, the White trap has been the traditional method of collecting entomopathogenic nematodes. In the White trap, infected insect cadavers are placed within a topless petri plate and the plate is placed in a tray of water. As the nematodes complete their development and emerge to seek new insect hosts, they exit the cadaver into the tray of water and are unable to escape. Nematodes are thus collected in the tray water. Scale-up of harvesting has consisted of simply providing larger White traps, usually by placing several dishes within a large tray. Emerging infective juveniles pass through the disk and settle at the funnel bottom where they are collected by opening the stopcock.

In the natural lifecycle of entomopathogenic nematodes, juveniles infect and kill host insects, multiply and grow to adulthood inside insect cadavers, then produce new infective juveniles that burst from the cadavers and exit into the surrounding medium. In the absence of expensive centrifuges, infective juveniles have traditionally been allowed to settle by gravity, the supernatant is then poured off and either replaced by freshwater or the nematodes are concentrated into a paste for formulation. The settling process in a large volume is time consuming, resulting in anoxic conditions which stress the nematodes.

Therefore, the need exists for improved apparatus and methods for in vivo separation of insecticidal nematodes from bacteria, insect cadavers and debris associated with growth medium used in the harvesting of infective juvenile nematodes.

SUMMARY OF THE INVENTION

An object of the present invention is to provide an apparatus for the separation of nematodes from a suspension comprising a reservoir tank for holding nematode suspension; a distribution manifold for dividing the flow of the nematode suspension into individual streams; a control valve for regulating flow; a screen; and a nematode slurry collector (hereinafter referred to as collector).

Another object of the present invention is to provide a method for the production of a nematode slurry comprising introducing a nematode suspension into an apparatus comprising a reservoir tank for holding nematode suspension; a distribution manifold for dividing the flow of the nematode suspension into individual streams; a control valve for regulating flow; a screen; and a collector for collecting nematode slurry, wherein the nematode suspension is present in a holding tank. Then, pumping the nematode suspension from the holding tank into the reservoir tank; feeding the nematode suspension into a distribution manifold; flowing nematode suspension out small openings on the distribution manifold onto a screen; passing the nematode suspension through the screen into a collector, wherein the nematodes are deflected by the screen but do not pass through the screen, and wherein the waste water passes through the screen; discarding waste water containing bacteria and debris through an outlet pipe; collecting nematodes on the screen to produce a nematode slurry; and collecting the nematode slurry in a collector.

BRIEF DESCRIPTION OF THE DRAWINGS

FIG. 1 is an isometric view of a preferred embodiment of a separator apparatus according to the present invention.

DETAILED DESCRIPTION OF THE INVENTION

The present invention provides an apparatus and method for separating harvested nematodes from bacteria, and debris such as insect carcasses, residues, litter, and particulate waste commonly associated with efficient mass production of nematodes. Harvested nematodes are any At entomopathogenic nematode, including any one of the more than 30 species of Steinernema and Heterorhabditis from culture medium or other liquids. It is preferred that the harvested nematodes are infective juvenile nematodes. The basic apparatus for the separation of nematodes from a suspension comprises a reservoir tank for holding nematode suspensions, preferably freshly harvested infective juvenile nematode suspension; a distribution manifold for dividing the flow of the nematode suspension into individual streams; a control valve for regulating flow; a screen; and a collector for collecting nematode slurry.

The method of the present invention comprises six basic steps: (1) pumping the nematode suspension from the holding tank into the reservoir tank; (2) feeding the nematode suspension into a distribution manifold; (3) flowing nematode suspension out small openings on the distribution manifold onto a screen; (4) deflecting the nematode suspension off of the surface of the screen so that a nematode slurry flows down the screen surface into a collector, and waste water passes through the screen; (5) discarding waste water containing bacteria and debris through an outlet pipe and (6) collecting nematodes on the screen to produce a nematode slurry in a collector.

In a preferred embodiment of the present invention, all six basic steps are accomplished through the use of an apparatus which continually separates the nematode suspension from bacteria and debris present in the suspension. Alternative embodiments of this apparatus will be readily understood from the detailed description that follows.

In one embodiment, the resultant aqueous solution or other nematode suspension from an in vivo juvenile nematode harvest device, system or apparatus comprising the harvested nematodes flows into the continuous separation apparatus of the present invention and in a single pass results in a viable juvenile nematode concentration with greater than 50 percent of the bacteria and debris such as insect carcasses, sand, litter and particulate waste removed, more preferably greater than 70 percent of the bacteria and debris such as insect carcasses, sand, litter and particulate waste are removed, and most preferably greater than 85 percent of the bacteria and debris such as insect carcasses, sand, litter and particulate waste are removed.

In a preferred embodiment, the apparatus is used to separate the freshly harvested nematodes in suspension from bacteria, adult nematodes, host cadaver frass and other contaminants present in the suspension. Leached bacteria, pigments, and cadaver residues must be reduced or removed from the nematode suspension to protect the viability of the juvenile nematodes. The bacteria, decaying adults and cadaver debris compete with the infective juvenile nematodes for oxygen and therefore must be removed from the harvested infective juvenile nematode suspension as soon as possible. The continuous separation apparatus of the present invention uses continuous deflection as a means for separation of the juvenile nematodes. A particulate-bearing stream of liquid or air is deflected by a permeable barrier in such a manner that the stream passes through the barrier and the particulates are deflected by its surface. A continuous water flow is directed at an obliquely oriented separation screen which, together with a low head differential across the screen face, keeps it free from blockage. Water escapes through the screen, while litter, fine sand, and other particulate debris are deflected into a collection sump, and later discarded. The apparatus as depicted in FIG. 1, washes and concentrates the nematode suspension, and removes the bacterial suspension. Additional water may be added to dilute the original suspension for further cleaning. Suspended nematodes from the holding tank are first pumped into a reservoir tank 1 through an inlet tube or pipe 9 and then gravity-fed to a distribution manifold 2, which divides the flow into at least one nematode suspension stream, hereinafter referred to as nematode stream. A connector comprising a control valve 3 connects the reservoir tank to the distribution manifold, the control valve regulates the flow of nematode suspension flowing into the distribution manifold. The connector may be a pipe, flexible tubing or other suitable component. The reservoir tank 1 is preferably shaped with a conical-bottom. In a preferred embodiment, each nematode stream averages a flow of about 700 ml/min, although the rate of flow may be variably adjusted depending upon the application. The flow is controlled by the control valve 3 above the distribution manifold 2. In a further preferred embodiment, streams are directed onto a 43.2 mm stainless steel screen 4 with an upper and lower surface and oriented at a 38° angle. The angle of the screen may be variably adjusted depending upon the size of the openings in the screen. Wastewater, containing the bacteria passes through the screen onto a waste water collector 6 and is then discarded through an outlet pipe 8, attached to the waste water collector 6, whereas nematodes are deflected and collect on the upper screen surface 4. A concentrated nematode slurry is generated which slowly flows by gravity off the screen, to a collector 5, and into a storage tank. In a preferred embodiment the collector 5 is a pipe which is half or partially open in order to receive the nematode slurry from the screen and the collector directs the nematode slurry on a route to the temporary storage tank. The nematode slurry can be further washed and concentrated by multiple passages through the continuous separation apparatus, water may be added to dilute the concentrated slurry as required to facilitate the flow of the nematode slurry during the multiple passes through the continuous separation apparatus. The remixing of the waste water and the concentrated nematode slurry is prevented by a deflection plate 10 as shown on FIG. 1.

The reservoir tank 1 is attached to or resting upon a support base 11 oriented so that an inlet tube or pipe is attached to the distribution manifold 2. The distribution manifold may be any shape but is preferably cylindrical in shape, when viewed in cross section, with a top side and a bottom side and is closed or plugged at both ends of the cylinder. The bottom side of the distribution manifold 2 is perforated or has outlet holes present, allowing the flow of the harvested nematode suspension from the reservoir tank 1 to be gravity-fed into the distribution manifold 2 and to flow out small openings on the bottom side of the distribution manifold resulting in at least one and preferably several smaller nematode streams comprising the nematode suspension which flow from the bottom side of the distribution manifold onto a screen attached in a secured or rotatable manner to the base 11 beneath the distribution manifold so that the screen may be held in at a desirable angle to the nematode stream flow from the bottom side of the distribution manifold. The flow of the nematode streams may be controlled by a valve 3 above the distribution manifold 2. In a further preferred embodiment, the nematode streams are directed onto a stainless steel screen 4, preferably 43.2 mm, with an upper and lower surface and oriented at a 38° angle. Both the screen size and the orientation angle of the screen may be variably adjusted depending upon the nematode species being cleaned and concentrated. Nematode suspension containing nematodes, and various unwanted materials such as bacteria and debris such as sand, cadaver residues, or pigments pass through the screen 4 onto a waste water collector 6 resting beneath the screen 4. The waste water collector 6 is oriented to catch the flow from the screen. The waste water containing bacteria and debris is then discarded through an outlet pipe 8, whereas nematodes are deflected and collect on the upper screen surface resulting in a nematode slurry 4. A concentrated nematode slurry is generated which slowly flows by gravity off the screen, and into a collector 5, and then further into a storage tank or other collection device via an outlet tube 7. In a preferred embodiment the collector 5 is half or partially open in order to receive the nematode slurry from the screen and further direct the nematode slurry to a temporary storage area or tank. The slurry can be further washed and concentrated by multiple passes through the continuous separation apparatus. The remixing of the waste water and the concentrated suspension is prevented by a deflection plate 10.

The materials used in the invention for constructing the reservoir tank, distribution manifold, control valve, screen, and collector for collecting nematode slurry, should be inert materials that are non-toxic to the nematodes. Such materials include, but are not limited to, aluminum, stainless steel, plastics, glass, Teflon, and non-metallic substances.

Supporting structures (e.g., base structure housings and support beams to hold the apparatus in place) that do not come into contact with the nematodes may comprise any commonly available construction materials.

The continuous separation apparatus concentration efficiency was tested three times using 20,000/ml suspension containing 3333.33±311.35 infective juvenile nematodes/ml. A single pass through the continuous separation apparatus removed 87.07±0.92 of the water and associated waste with a 4.45±2.0% loss of infective juvenile nematodes. The nematode suspension was concentrated from the initial 3333.33 to 25540.60±4370.60 infective juvenile nematodes/ml. After a third pass, approximately 97% of the water was removed with an accrued nematode loss of 11.05±2.54% and the nematodes were concentrated eight-fold to 269701±15111.42 infective juveniles/ml. The wastewater may be cycled through the apparatus again to recapture any lost nematodes and the nematodes should be formulated or resuspended for aqueous storage.

The results described above were obtained for a suspension containing *H. bacteriophora*. The continuous separation apparatus is equally efficient in separation of *S. carpocapsae*, as the infective juveniles of these two species are similar in size (558 and 588 mm respectively). The continuous separation apparatus is also effective for other species including but not limited to *S. glaseri* at 1030 mm, with slight alterations to the screen mesh opening size and/or screen angle of the continuous separation apparatus as would be known to one of skill in the art. In another embodiment, the continuous separation apparatus of the present invention incorporates interchangeable or pivoting screens into the design to accommodate different nematode species.

What is claimed:

1. An apparatus for the separation of nematodes from a suspension comprising:

a.) a reservoir tank for holding a nematode suspension;

b.) a distribution manifold for dividing the flow of the nematode suspension into at least one nematode suspension stream;

c.) a control valve affixed to a connector linking the reservoir tank to the distribution manifold, said control valve regulating the flow of the nematode suspension flowing into the distribution manifold;

d.) a screen attached to a support base, said screen located beneath the distribution manifold at a selected angle to the nematode suspension stream so that nematodes are collected on the screen to generate a concentrated nematode slurry; and e.) a collector located adjacent to the screen in a manner which allows the concentrated nematode slurry to flow from the screen into the collector.

2. The apparatus of claim 1 wherein the screen is oriented at a 38 degree angle to the nematode stream.

3. A method for the production of a nematode slurry comprising:

a.) introducing a nematode suspension into the apparatus of claim 1, wherein the nematode suspension is present in a holding tank;

b.) pumping the nematode suspension from the holding tank into the reservoir tank;

c.) feeding the nematode suspension from the reservoir tank through a connector into a distribution manifold;

d.) flowing nematode suspension out small openings on the distribution manifold onto a screen;

e.) passing the nematode suspension through the screen into a collector, wherein the nematodes are deflected by the screen but do not pass through the screen, and wherein the waste water passes through the screen;

f.) discarding waste water containing bacteria and debris through an outlet pipe;

g.) collecting nematodes on the screen to produce a nematode slurry; and h.) collecting the nematode slurry in a collector.

4. The method of claim 3 wherein the nematode slurry in the collector is further flowed into a storage tank or collection device via an outlet tube.

5. The method of claim 3 wherein the waste water is prevented from remixing with the nematode slurry by a deflection plate.

6. The method of claim 3 wherein the nematode in the nematode suspension is a species of Steinernema or Heterorhabditis.

* * * * *